United States Patent
Kubo et al.

(10) Patent No.: US 7,442,246 B2
(45) Date of Patent: Oct. 28, 2008

(54) PHOSPHATE-BASED DENTAL INVESTING MATERIAL

(75) Inventors: Fuminobu Kubo, Katano (JP); Shinko Sato, Katano (JP); Takayuki Ueno, Katano (JP); Haruhiko Horiuchi, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 11/761,013

(22) Filed: Jun. 11, 2007

(65) Prior Publication Data

US 2007/0283850 A1    Dec. 13, 2007

(30) Foreign Application Priority Data

Jun. 13, 2006    (JP)   ............... 2006-163290

(51) Int. Cl.
*A61K 6/00*    (2006.01)
*C04B 12/02*    (2006.01)

(52) U.S. Cl. .................. 106/35; 106/38.9; 106/691
(58) Field of Classification Search .................. 106/35, 106/691, 38.9
See application file for complete search history.

(56) References Cited

U.S. PATENT DOCUMENTS 5,968,253 A * 10/1999 Poser et al. .................. 106/691
7,083,672 B2 * 8/2006 Wagh et al. .................. 106/35

FOREIGN PATENT DOCUMENTS

| EP | 0 868 896 A2 | 10/1998 |
| EP | 1364925 A1 * | 11/2003 |
| JP | 6-336409 | 12/1994 |

OTHER PUBLICATIONS

HJ Mueller, et al., "Surfactant-containing phosphate investments", Dent Mater, vol. 2, No. 1, Feb. 1986, pp. 42-44.
Database WPI Week 199732, Derwent Publications Ltd., XP002448234, JP 09 141387 A, Jun. 3, 1997.
Database WPI Week 198447, Derwent Publications Ltd., XP002448235, JP 59 181204 A, Oct. 15, 1984.

* cited by examiner

Primary Examiner—Anthony J Green
(74) Attorney, Agent, or Firm—Oblon, Spivak, McClelland, Maier & Neustadt, P.C.

(57) ABSTRACT

In order to produce a dental cast product having the flat surface, by blending a dispersant with a phosphate-based investing material to improve the dispersability of an aggregate powder and a binder powder so as to prevent a agglomeration of the aggregate powder and the binder powder thereby forming a wall surface of an cavity in a mold to be flat, and also to make more various kinds of powders available for the aggregate powder without restriction to quartz, cristobalite and tridymite, the phosphate-based dental investing material comprising a mixed powder including an aggregate powder and a phosphate-based binder powder, and a liquid, with an alkaline metal salt of phosphoric acid being added to at least one of the mixed powder and the liquid.

21 Claims, No Drawings

PHOSPHATE-BASED DENTAL INVESTING MATERIAL

BACKGROUND OF THE INVENTION

1. Field of the Invention

The present invention relates to a phosphate-based dental investing material used for molding a dental mold, and the material is used for a mold for casting a dental metal product such as a crown or the like so as to cast the metal product having a smooth surface.

2. Description of the Conventional Art

As for a dental investing material, a gypsum-based investing material and a phosphate-based investing material have been known. The gypsum-based investing material is preferably used since an investing operation and a digging operation of a cast product are easy. However, gypsum is decomposed at 700 degree C. or more under the existence of carbon contained in a wax or the like, and thus cannot be used for casting an alloy having a high melting point such as an alloy for porcelain fused to metal. Therefore, when an alloy having a high melting point is cast, a phosphate-based investing material has been generally used. Further, in order to save the time necessary for the preheating of a mold and the incineration of a wax pattern, quick heating has been widely used in recent years. In the quick heating, an investing material, in which a wax pattern is invested, is directly taken into a furnace at a temperature of 800 to 900 degree C. together with a cast ring.

As the phosphate-based investing material capable of quickly heating, Japanese Patent Application Laid Open No. 06(1994)-336409 discloses an investing material including a refractory material and a phosphate-based binder (for example, a mixing material of magnesia clinker and ammonium primary phosphate), where tridymite is added to quartz and/or cristobalite used as the refractory material. As for the investing material indicated in this patent document, a part of a quartz and/or cristobalite having excellent properties to compensate casting contraction of metal is replaced by tridymite having comparatively low thermal expansion coefficient and no quick increase of the thermal expansion coefficient due to temperature increasing. Thus, crack does not occur even when quickly heating the material after investing, and the time necessary for the preheating of a mold and the incineration of a wax pattern can be largely shortened.

However, when a mold strength increases by decreasing the mixing ratio of a liquid in order to prevent the crack or surface peeling of a mold, flowability of an investing material decreases, and thus the investing operation becomes hard. Further, when a refractory material having a large particle diameter is used as an aggregate powder so as to improve the flowability, there is a problem that a cast surface is roughed. When the particle diameter of the aggregate powder is made small, the flowability decreases, so that the aggregate powder coagulates so as to become a lump having a larger diameter than that of the refractory material powder. Thus, the surface roughness of a cast product increases so that it is necessary to polish the surface of the cast product in order to decrease the surface roughness. However, polishing takes a long time, and it is uneconomical when casting a noble-metals product especially. Furthermore, the refractory material is restricted in quartz, cristobalite, and tridymite.

SUMMARY OF THE INVENTION

The present invention makes it possible to produce a dental cast product having a smooth surface, that is, a smooth cast surface, by blending a dispersant to a phosphate-based investing material so as to prevent agglomerating of the aggregate powder and the binder powder, where the dispersant improves dispersibility of the aggregate powder and the binder powder, so as to form the smooth wall surface of a cavity in a mold. Further, according to the present invention, the aggregate powder is not necessarily restricted to quartz, cristobalite, and tridymite.

A phosphate-based dental investing material according to the present invention includes a mixed powder which is mixed an aggregate powder and a phosphate-based binder powder, and a liquid, and an alkaline metal salt of phosphoric acid is added to at least one of the powder and the liquid.

In the present invention, an alkaline metal salt of phosphoric acid is added to a phosphate-based dental investing material. The alkaline metal salt of phosphoric acid works as a dispersant to prevent to agglomerating of the aggregate powder and the binder powder. Thus, when a wax pattern is invested, the aggregate powder and the binder powder are not agglomerated on the wall surface of a mold surrounding the wax pattern but precisely arranged along the surface of the pattern. That is, the inner wall surface of the mold is formed to have a smooth surface on which the surface roughness is determined by only the particle diameters of the aggregate powder and the binder powder. Thus, since the smooth surface is copied to the surface of a cast product, a cast product having a smooth cast surface can be obtained.

The alkaline metal salt of phosphoric acid is not restricted especially, but typical examples are potassium orthophosphate, potassium metaphosphate, potassium pyrophosphate, sodium primary phosphate, dibasic sodium phosphate, sodium tertiary phosphate, sodium hexametaphosphate, sodium pyrophosphate, sodium tripolyphosphate, potassium tripolyphosphate, sodium tetrametaphosphate and the like.

In addition, an arbitrary refractory material to be used for a dental investing material is used as the aggregate powder. For example, quartz, cristobalite, tridymite, alumina, zircon, zirconia, mullite, spinel and the like can be used. As for these aggregate powders, any one kind can be used independently, or two or more kinds can be mixed to be used. So, the powders are suitably selected depending on an objective of the cast. Further, a powder mixture of phosphate and a basic metal oxide is used as the binder powder. Furthermore, a colloidal silica solution is used as the liquid like the conventional technique.

The mixed powder is mixed the aggregate powder and the binder powder, and the liquid to constitute the phosphate-based investing material are mixed to be used at the time of casting. In this case, the blending amount of the aggregate powder is 70 to 90 wt. % to the whole mixed powder and the residual amount is the blending amount of the binder powder. 10 to 30 mL of the liquid is blended with 100 g of the mixed powder. Further, it is preferable that the alkali metal salt of phosphoric acid added as the dispersant in the present invention is mixed beforehand with at least one of the mixed powder including the aggregate powder and the binder powder, and the liquid. Then, the mixed powder and the liquid is mixed at the time of casting.

As for the blending amount of the dispersant, that is, the alkali metal salt of phosphoric acid, 0.1 to 2.0 wt. parts of the dispersant to 100 wt. parts of the mixed powder are preferable when it is mixed beforehand with the mixed powder. Further, 0.1 to 2.0 wt. parts of the dispersant to 100 wt. parts of the liquid is preferable when it is mixed beforehand with the liquid. The dispersant may be mixed beforehand with both of the mixed powder and the liquid. When the adding amount of the alkali metal salt of phosphoric acid is less than the above-described range, the dispersing effect caused by adding the dispersant cannot be obtained, so that a cast product having the smooth surface cannot be obtained. When the adding amount is excessive to the above-described range, the dispersing effect is not varied, and it is uneconomical. Besides, the colloidal silica solution stored in the liquid is gelled so that it is not proper.

According to the present invention, since the alkali metal salt of phosphoric acid is added to the phosphate-based dental investing material, the agglomeration of the aggregate powder and the binder powder to constitute the dental investing material can be prevented. Thus, the wall in a cavity of the mold in which the investing material is invested becomes smooth. Therefore, the surface of a cast product can be formed smooth so that the process for polishing the surface of the cast product is not necessary, while the polishing is needed in the conventional technique. Thus, the required time for casting can be shortened. Further, a casting metal can be also saved, and the refractory material to be used is not restricted. In particular, according to the present invention, since the blending amount of the alkali metal salt of phosphoric acid is restricted, the effect caused by blending the alkali metal salt can be easily obtained, and it is economical.

DETAILED DESCRIPTION OF PREFERRED EMBODIMENT

First Embodiment

A mixed powder including an aggregate powder and a binder powder, and a liquid are prepared. As the aggregate powder, a powder including a refractory material selected from one or more of refractory materials, for example, quartz, cristobalite, tridymite, alumina, zircon, zirconia, mullite, and spinel, is prepared. As the binder powder, a powder mixture of a basic metal oxide (for example, magnesia clinker) and phosphate (for example, monobasic ammonium phosphate) is prepared. As a liquid, a colloidal silica solution (the silica concentration is 10 to 40%, the silica particle diameter is 8 to 100 nm) is used like the conventional technique. When the mixed powder and the liquid are mixed at the time of casting, the blending amount of the aggregate powder is 70 to 90 wt. % to the total amount of the aggregate powder and the binder powder, that is, to the whole mixed powder, and the residual amount is the blending amount of the blinder powder. 10 to 30 mL of the liquid is mixed with 100 g of the mixed powder.

On the other hand, as the dispersant of the mixed powder, an alkali metal salt of phosphoric acid is prepared. For example, any one of potassium orthophosphate, potassium meta-phosphate, potassium pyrophosphate, sodium primary phosphate, dibasic sodium phosphate, sodium tertiary phosphate, sodium hexameta-phosphate, sodium pyrophosphate, sodium tripolyphosphate, potassium tripolyphosphate, sodium tetrameta-phosphate is prepared. Further, 0.1 to 2.0 wt. parts of the alkali metal salt of phosphoric acid are mixed beforehand with 100 wt. parts of the mixed powder and after mixed with the liquid to be used for investing a pattern when a casting operation starts.

Accordingly, the phosphate-based investing material is obtained by kneading the mixed powder with the liquid, in which the mixed powder has been made by mixing the dispersant (the alkali metal salt of phosphoric acid) beforehand to the mixed powder including the aggregate powder and the binder powder. Then, the phosphate-based investing material is taken into a ring for casting, and a wax pattern is invested. After 20 to 30 minutes, the ring is taken into a furnace at 800 to 900 degree C. so as to incinerate and remove the wax pattern. As a result of this, a mold having a smooth cavity surface is obtained without surface peeling and crack. Then, a dental metal is cast so as to obtain a metal product having a smooth surface.

Second Embodiment

A mixed powder including an aggregate powder and a binder powder, a colloidal silica solution and a dispersant are prepared like the above-described first embodiment. The dispersant is mixed and dissolved with the colloidal silica solution so as to make a liquid. The blending amount of the dispersant is 0.1 to 2.0 wt. parts of the dispersant to 100 wt. parts of the colloidal silica solution. The mixing ratio of the aggregate powder and the binder powder and the liquid is same as in the above-described first embodiment. Then, at the time of starting the casting operation, the liquid in which the dispersant is dissolved in the colloidal silica is mixed with the mixed powder including the aggregate powder and the binder powder so as to be formed as a mold. Then, the casting operation similar to that of the first embodiment is carried out.

EXAMPLES

As an aggregate material, cristobalite (200 mesh-under, that is, all of the power passes the screen having 200 mesh), quartz A (200 mesh-under), quartz B (an average particle diameter was 70μm), and zircon (200 mesh-under) were prepared. As a binder, a mixture of magnesia clinker and ammonium primary phosphate, where the mixing ratio was 50:50, was prepared. As a liquid, colloidal silica sol (the particle diameter of colloidal silica was 40 to 60 nm, the concentration was 20%) was prepared. As a dispersant (an alkali metal salt of phosphoric acid), sodium hexameta-phosphate, sodium orthophosphate, sodium pyrophosphate, and potassium tripolyphosphate were prepared.

The investing materials of Examples 1 to 14 and Comparative examples 1 to 7 were obtained using the mixed powder including the aggregate powder and the binder powder, the liquid and the dispersant. The mixing ratios (the units were weight parts) were shown in the following Tables 1 to 3. Examples 1 to 7 in Table 1 show the materials in which the dispersant was blended with the mixed powder beforehand. Examples 8 to 14 in Table 2 show the materials in which the dispersant was blended with the liquid beforehand. In Comparative examples in Table 3, Comparative examples 1 and 2 show an example in which the dispersant were not used at all, Comparative examples 3 and 4 show an examples in which the dispersant was blended with the mixed powder, and Comparative examples 5, 6 and 7 show an example in which the dispersant was blended with the liquid.

TABLE 1

|  |  | Examples |  |  |  |  |  |  |
|---|---|---|---|---|---|---|---|---|
|  |  | 1 | 2 | 3 | 4 | 5 | 6 | 7 |
| Mixed Powder | Aggregate powder |  |  |  |  |  |  |  |
|  | Cristobalite | 20 | 20 | 20 | 20 | 20 | 20 | 20 |
|  | Quartz A | 50 | 50 | 50 | 50 | 50 | 50 | 50 |
|  | Quartz B | — | — | — | — | — | — | — |
|  | Zircon | 10 | 10 | 10 | 10 | 10 | 10 | 10 |
|  | Binder powder |  |  |  |  |  |  |  |
|  | Magnesia clinker | 10 | 10 | 10 | 10 | 10 | 10 | 10 |
|  | Ammonium primary phosphate | 10 | 10 | 10 | 10 | 10 | 10 | 10 |
|  | Dispersant |  |  |  |  |  |  |  |
|  | Sodium hexameta-phosphate | 0.1 | 1.0 | — | — | — | — | — |
|  | Sodium orthophosphate | — | — | 0.5 | — | — | — | 0.5 |
|  | Sodium pyrophosphate | — | — | — | 0.5 | 2.0 | — | 0.5 |
|  | Potassium tripolyphosphate | — | — | — | — | — | 1.0 | — |
| Liquid | Colloidal silica solution | 100 | 100 | 100 | 100 | 100 | 100 | 100 |

TABLE 2

|  |  | Examples |  |  |  |  |  |  |
|---|---|---|---|---|---|---|---|---|
|  |  | 8 | 9 | 10 | 11 | 12 | 13 | 14 |
| Mixed Powder | Aggregate powder |  |  |  |  |  |  |  |
|  | Cristobalite | 20 | 20 | 20 | 20 | 20 | 20 | 20 |
|  | Quartz A | 50 | 50 | 50 | 50 | 50 | 50 | 50 |
|  | Quartz B | — | — | — | — | — | — | — |
|  | Zircon | 10 | 10 | 10 | 10 | 10 | 10 | 10 |
|  | Binder powder |  |  |  |  |  |  |  |
|  | Magnesia clinker | 10 | 10 | 10 | 10 | 10 | 10 | 10 |
|  | Ammonium primary phosphate | 10 | 10 | 10 | 10 | 10 | 10 | 10 |
| Liquid | Colloidal silica solution | 100 | 100 | 100 | 100 | 100 | 100 | 100 |
|  | Dispersant |  |  |  |  |  |  |  |
|  | Sodium orthophosphate | 0.1 | 0.5 | — | — | — | — | 0.5 |
|  | Sodium pyrophosphate | — | — | 0.5 | 1.0 | 2.0 | — | 0.5 |
|  | Potassium tripolyphosphate | — | — | — | — | — | 1.0 | — |

TABLE 3

|  |  | Comparative examples |  |  |  |  |  |  |
|---|---|---|---|---|---|---|---|---|
|  |  | 1 | 2 | 3 | 4 | 5 | 6 | 7 |
| Mixed Powder | Aggregate powedr |  |  |  |  |  |  |  |
|  | Cristobalite | 20 | 20 | 20 | 20 | 20 | 20 | 20 |
|  | Quartz A | 50 | 40 | 50 | 50 | 50 | 50 | 50 |
|  | Quartz B | — | 10 | — | — | — | — | — |
|  | Zircon | 10 | 10 | 10 | 10 | 10 | 10 | 10 |
|  | Binder powder |  |  |  |  |  |  |  |
|  | Magnesia clinker | 10 | 10 | 10 | 10 | 10 | 10 | 10 |
|  | Ammonium primary phosphate | 10 | 10 | 10 | 10 | 10 | 10 | 10 |
|  | Dispersant |  |  |  |  |  |  |  |
|  | Sodium hexameta-phosphate | — | — | — | — | — | — | — |
|  | Sodium orthophosphate | — | — | 5 | — | — | — | — |
|  | Sodium pyrophosphate | — | — | — | 5 | — | — | — |
|  | Potassium tripolyphosphate | — | — | — | — | — | — | — |
| Liquid | Colloidal silica solution | 100 | 100 | 100 | 100 | 100 | 100 | 100 |
|  | Dispersant |  |  |  |  |  |  |  |
|  | Sodium | — | — | — | — | — | 3 | — |

The investing materials of Examples 1 to 14 and Comparative examples 1 to 7 were subjected to a flowability test, a crack test of a mold, and a casting test, and stabilities of the liquids were compared. These results were shown in Table 4. However, the mixing ratio of the liquid to the mixed powder was 24 mL/100 g. The mixing was carried out by hand mixing for 15 seconds and vacuum mixing for 60 seconds, using Vacuum Mixer VM1 produced by GC Corporation. The temperature of a furnace was 800 degree C., and these samples were taken into the furnace after 20 minutes from investing.

Flowability Test

The flowability test was carried out based on Section 5.4 Flowability in "Phosphate-based Investing Material for Dental Casting", JIS T 6608 (2001), which was described in Japanese Industrial Standard. The material having the flowability of 135 mm or more was determined as "Preferable".

Crack Test of a Mold

The crack test of a mold was carried out based on Section 5.8 Observation of Crack and Peeling in "Phosphate-based Investing Material for Dental Casting", JIS T 6608 (2001), which was described in Japanese Industrial Standard. The material not having the crack and peeling was determined as "○", the material having one or both of the crack and peeling was determined as "x".

Casting Test

Casting was carried out by the steps of: producing a pattern of MOD using a metal mold; investing the pattern into Second Ring which was rolled by one sheet of "New Casting Linear" No. 12, where the Second Ring and "New Casting Linear" No. 12 were produced by GC Corporation; taking the ring into a furnace at 800 degree C. after 20 minutes from investing; leaving the ring in the furnace for 30 minutes so as to incinerate the pattern; taking out the ring after incinerating; and casting a cast body by using "Super Cascom", which was a vacuum pressurized casting machine produced by DEN-KEN Corporation. As a metal for casting, "Casting Bond M.C., 50" produced by GC Corporation was used. After the mold is cooled, the cast body was dug out, and dipped in an aqueous solution of hydrofluoric acid so as to remove the investing material on the metal surface. Then, an arithmetic average roughness (Ra) of the surface of the cast body was measured using "SurfCom", which was a surface roughness gauge produced by Tokyo Seimitsu Corporation. The cast body having the surface roughness of 1.2 μm or less was determined as "Preferable". As for fitness of the cast body, the cast body was returned to the metal mold, and was determined as "Preferable", "Large", and "Small".

Stability of a Liquid 30 mL of a liquid was taken into a sample tube having the capacity of 50 mL, and stored for one week in a thermostatic chamber at the temperature of 23 degree C. Then, the state of the liquid was observed. The liquids were compared with the liquids not blended with the dispersant, and evaluated as "○" when the states were similar, "Δ" when the liquid viscosity increased, and "x" when the liquid was gelled.

TABLE 4

|  | Flowability test | Crack test | Casting test Surface roughness | Fitness | Stability of Liquid |
|---|---|---|---|---|---|
| Example 1 | 137 | ○ | 1.0 | Preferable | ○ |
| Example 2 | 140 | ○ | 1.0 | Preferable | ○ |
| Example 3 | 141 | ○ | 0.9 | Preferable | ○ |
| Example 4 | 140 | ○ | 1.1 | Preferable | ○ |
| Example 5 | 138 | ○ | 1.0 | Preferable | ○ |
| Example 6 | 140 | ○ | 0.9 | Preferable | ○ |
| Example 7 | 141 | ○ | 1.0 | Preferable | ○ |
| Example 8 | 138 | ○ | 0.9 | Preferable | ○ |
| Example 9 | 140 | ○ | 1.0 | Preferable | ○ |
| Example 10 | 140 | ○ | 0.9 | Preferable | ○ |
| Example 11 | 143 | ○ | 1.0 | Preferable | ○ |
| Example 12 | 144 | ○ | 0.9 | Preferable | ○ |
| Example 13 | 143 | ○ | 0.8 | Preferable | ○ |
| Example 14 | 144 | ○ | 0.9 | Preferable | ○ |
| Comparative example 1 | 126 | ○ | 1.3 | Preferable | ○ |
| Comparative example 2 | 136 | ○ | 1.5 | Preferable | ○ |
| Comparative example 3 | 142 | ○ | 1.1 | Small | ○ |
| Comparative example 4 | 141 | ○ | 1.1 | Small | ○ |
| Comparative example 5 | 133 | X (Peeling) | 1.0 | Preferable | ○ |
| Comparative example 6 | 143 | ○ | 1.1 | Preferable | Δ |
| Comparative example 7 | 143 | ○ | 1.0 | Preferable | X |
| Comparative example 8 | 139 | X (Crack) | Cannot be cast due to the crack | | ○ |

In the table, Comparative example 8 was produced by changing the mixing ratio of Comparative example 1 to 26 mL/100 g.

As shown in Table 4, each of Examples 1 to 14 was excellent in flowability. Thus, there was no crack, and the surface roughness was 1.0 μm or less. The fitness at the time of returning the cast product to the metal mold was preferable, and the stability of the liquid was preferable. On the other hand, as for Comparative example 1, since the dispersant was not used, the flowability decreased, and thus the surface roughness was large. As for Comparative example 2, a part of the quartz A of Comparative example 1 was replaced by the quartz B having the large particle diameter, instead of using the dispersant. Thus, the flowability did not decreased, but the surface roughness increased. As for Comparative examples 3 and 4, the blending amount of the dispersant was excessive, so that the fitness decreased. As for Comparative example 5, the blending amount of the dispersant was too small, so that the flowability was low, and there occurred peeling in the crack test. As for Comparative examples 6 and 7, the dispersant was blended with the liquid, but the blending amount was excessive, and thus the preservability of the liquid decreased. As for Comparative example 8, the mixing ratio was large, and thus the strength of a mold decreased, the crack occurred due to quick heating, and casting cannot be carried out.

What is claimed is:

1. A phosphate-based dental investing material comprising a mixed powder comprising an aggregate powder and a phosphate-based binder powder,
a liquid, and
an alkaline metal salt of phosphoric acid,
wherein the alkaline metal salt of phosphoric acid is present in an amount of from 0.1 to 2.0 wt. parts to 100 wt. parts of the mixed powder, and the aggregate powder is at least one selected from the group consisting of quartz, cristobalite, tridymite, alumina, zircon, zirconia, mullite and spinel.

2. The phosphate-based dental investing material of claim 1, wherein the alkaline metal salt of phosphoric acid is at least one selected from the group consisting of potassium orthophosphate, potassium metaphosphate, potassium pyrophosphate, sodium orthophosphate, sodium primary phosphate, dibasic sodium phosphate, sodium tertiary phosphate, sodium hexametaphosphate, sodium pyrophosphate, sodium tripolyphosphate, potassium tripolyphosphate and sodium tetrametaphosphate.

3. A phosphate-based dental investing material comprising
a mixed powder comprising an aggregate powder and a phosphate-based binder powder,
a liquid, and
an alkaline metal salt of phosphoric acid,
wherein the alkaline metal salt of phosphoric acid is present in an amount of from 0.1 to 2.0 wt. parts to 100 wt. parts of the mixed powder, and the phosphate-based binder powder is a powder mixture of a metal oxide and phosphate.

4. The phosphate-based dental investing material of claim 3, wherein the metal oxide is magnesia clinker and the phosphate is monobasic ammonium phosphate.

5. The phosphate-based dental investing material of claim 3, wherein the alkaline metal salt of phosphoric acid is at least one selected from the group consisting of potassium orthophosphate, potassium metaphosphate, potassium pyrophosphate, sodium orthophosphate, sodium primary phosphate, dibasic sodium phosphate, sodium tertiary phosphate, sodium hexametaphosphate, sodium pyrophosphate, sodium tripolyphosphate, potassium tripolyphosphate and sodium tetrametaphosphate.

6. A phosphate-based dental investing material comprising
a mixed powder comprising an aggregate powder and a phosphate-based binder powder,
a liquid, and
an alkaline metal salt of phosphoric acid,
wherein the alkaline metal salt of phosphoric acid is present in an amount of from 0.1 to 2.0 wt. parts to 100 wt. parts of the mixed powder, and the liquid is a colloidal silica solution.

7. The phosphate-based dental investing material of claim 6, wherein the alkaline metal salt of phosphoric acid is at least one selected from the group consisting of potassium orthophosphate, potassium metaphosphate, potassium pyrophosphate, sodium orthophosphate, sodium primary phosphate, dibasic sodium phosphate, sodium tertiary phosphate, sodium hexametaphosphate, sodium pyrophosphate, sodium tripolyphosphate, potassium tripolyphosphate and sodium tetrametaphosphate.

8. A phosphate-based dental investing material comprising
a mixed powder comprising an aggregate powder and a phosphate-based binder powder,
a liquid, and
an alkaline metal salt of phosphoric acid,
wherein the alkaline metal salt of phosphoric acid is present in an amount of from 0.1 to 2.0 wt. parts to 100 wt. parts of the liquid, and the aggregate powder is at least one selected from the group consisting of quartz, cristobalite, tridymite, alumina, zircon, zirconia, mullite and spinel.

9. The phosphate-based dental investing material of claim 8, wherein the alkaline metal salt of phosphoric acid is at least one selected from the group consisting of potassium orthophosphate, potassium metaphosphate, potassium pyrophosphate, sodium orthophosphate, sodium primary phosphate, dibasic sodium phosphate, sodium tertiary phosphate, sodium hexametaphosphate, sodium pyrophosphate, sodium tripolyphosphate, potassium tripolyphosphate and sodium tetrametaphosphate.

10. A phosphate-based dental investing material comprising
a mixed powder comprising an aggregate powder and a phosphate-based binder powder,
a liquid, and
an alkaline metal salt of phosphoric acid,
wherein the alkaline metal salt of phosphoric acid is present in an amount of from 0.1 to 2.0 wt. parts to 100 wt. parts of the liquid, and the phosphate-based binder powder is a powder mixture of a metal oxide and phosphate.

11. The phosphate-based dental investing material of claim 10, wherein the metal oxide is magnesia clinker and the phosphate is monobasic ammonium phosphate.

12. The phosphate-based dental investing material of claim 10, wherein the alkaline metal salt of phosphoric acid is at least one selected from the group consisting of potassium orthophosphate, potassium metaphosphate, potassium pyrophosphate, sodium orthophosphate, sodium primary phosphate, dibasic sodium phosphate, sodium tertiary phosphate, sodium hexametaphosphate, sodium pyrophosphate, sodium tripolyphosphate, potassium tripolyphosphate and sodium tetrametaphosphate.

13. A phosphate-based dental investing material comprising
a mixed powder comprising an aggregate powder and a phosphate-based binder powder,
a liquid, and
an alkaline metal salt of phosphoric acid,
wherein the alkaline metal salt of phosphoric acid is present in an amount of from 0.1 to 2.0 wt. parts to 100 wt. parts of the liquid, and the liquid is a colloidal silica solution.

14. The phosphate-based dental investing material of claim 13, wherein the alkaline metal salt of phosphoric acid is at least one selected from the group consisting of potassium orthophosphate, potassium metaphosphate, potassium pyrophosphate, sodium orthophosphate, sodium primary phosphate, dibasic sodium phosphate, sodium tertiary phosphate, sodium hexametaphosphate, sodium pyrophosphate, sodium tripolyphosphate, potassium tripolyphosphate and sodium tetrametaphosphate.

15. A phosphate-based dental investing material comprising
a mixed powder comprising an aggregate powder and a phosphate-based binder powder,
a liquid, and
an alkaline metal salt of phosphoric acid,
wherein the alkaline metal salt of phosphoric acid is present in an amount of from 0.1 to 2.0 wt. parts to 100 wt. parts of each of the mixed powder and the liquid, and the aggregate powder is at least one selected from the group consisting of quartz, cristobalite, tridymite, alumina, zircon, zirconia, mullite and spinel.

16. The phosphate-based dental investing material of claim 15, wherein the alkaline metal salt of phosphoric acid is at least one selected from the group consisting of potassium orthophosphate, potassium metaphosphate, potassium pyrophosphate, sodium orthophosphate, sodium primary phosphate, dibasic sodium phosphate, sodium tertiary phosphate, sodium hexametaphosphate, sodium pyrophosphate, sodium tripolyphosphate, potassium tripolyphosphate and sodium tetrametaphosphate.

17. A phosphate-based dental investing material comprising a mixed powder comprising an aggregate powder and a phosphate-based binder powder, a liquid, and an alkaline metal salt of phosphoric acid, wherein the alkaline metal salt of phosphoric acid is present in an amount of from 0.1 to 2.0 wt. parts to 100 wt. parts of each of the mixed powder and the liquid, and the phosphate-based binder powder is a powder mixture of a metal oxide and phosphate.

18. The phosphate-based dental investing material of claim 17, wherein the metal oxide is magnesia clinker and the phosphate is monobasic ammonium phosphate.

19. The phosphate-based dental investing material of claim 17, wherein the alkaline metal salt of phosphoric acid is at least one selected from the group consisting of potassium orthophosphate, potassium metaphosphate, potassium pyrophosphate, sodium orthophosphate, sodium primary phosphate, dibasic sodium phosphate, sodium tertiary phosphate, sodium hexametaphosphate, sodium pyrophosphate, sodium tripolyphosphate, potassium tripolyphosphate and sodium tetrametaphosphate.

20. A phosphate-based dental investing material comprising a mixed powder comprising an aggregate powder and a phosphate-based binder powder, a liquid, and an alkaline metal salt of phosphoric acid, wherein the alkaline metal salt of phosphoric acid is present in an amount of from 0.1 to 2.0 wt. parts to 100 wt. parts of each of the mixed powder and the liquid, and the liquid is a colloidal silica solution.

21. The phosphate-based dental investing material of claim 20, wherein the alkaline metal salt of phosphoric acid is at least one selected from the group consisting of potassium orthophosphate, potassium metaphosphate, potassium pyrophosphate, sodium orthophosphate, sodium primary phosphate, dibasic sodium phosphate, sodium tertiary phosphate, sodium hexametaphosphate, sodium pyrophosphate, sodium tripolyphosphate, potassium tripolyphosphate and sodium tetrametaphosphate.

* * * * *